United States Patent
Huang et al.

(10) Patent No.: US 11,112,366 B2
(45) Date of Patent: Sep. 7, 2021

(54) REAGENT AND KIT FOR ENHANCING CHEMILUMINESCENT REACTION

(71) Applicant: NATIONAL TAIWAN OCEAN UNIVERSITY, Keelung (TW)

(72) Inventors: Chih-Ching Huang, Keelung (TW); Chia-Wen Lien, Keelung (TW)

(73) Assignee: NATIONAL TAIWAN OCEAN UNIVERSITY, Keelung (TW)

(*) Notice: Subject to any disclaimer, the term of this patent is extended or adjusted under 35 U.S.C. 154(b) by 306 days.

(21) Appl. No.: 16/368,108

(22) Filed: Mar. 28, 2019

(65) Prior Publication Data

US 2020/0309707 A1 Oct. 1, 2020

(51) Int. Cl.
| | | |
|---|---|---|
| *G01N 21/76* | (2006.01) | |
| *C12Q 1/28* | (2006.01) | |
| *C07H 19/04* | (2006.01) | |
| *G01N 33/52* | (2006.01) | |
| *C07D 473/00* | (2006.01) | |
| *C07D 473/40* | (2006.01) | |
| *G01N 33/58* | (2006.01) | |

(52) U.S. Cl.
CPC .......... *G01N 21/76* (2013.01); *C07D 473/00* (2013.01); *C07D 473/40* (2013.01); *C07H 19/04* (2013.01); *C12Q 1/28* (2013.01); *G01N 33/52* (2013.01); *G01N 33/582* (2013.01)

(58) Field of Classification Search
None
See application file for complete search history.

(56) References Cited

U.S. PATENT DOCUMENTS

| | | | |
|---|---|---|---|
| 6,432,662 | B1 | 8/2002 | Davis et al. |
| 7,803,573 | B2 | 9/2010 | Della Ciana |
| 9,040,252 | B2 * | 5/2015 | Della Ciana ....... G01N 33/5306 435/7.92 |

FOREIGN PATENT DOCUMENTS

| | | |
|---|---|---|
| CN | 1661370 A | 8/2005 |
| EP | 1 962 095 A1 | 8/2008 |

OTHER PUBLICATIONS

Zhang el al. "Enhanced non-peroxidase chemiluminescence system determination of luminol and its derivatives," Fenxi Shiyanshi 1994, 13(2). (Year: 1994).*

* cited by examiner

*Primary Examiner* — Jeffrey S Lundgren
*Assistant Examiner* — Michael J Schmitt
(74) *Attorney, Agent, or Firm* — Birch, Stewart, Kolasch & Birch LLP (57) ABSTRACT

A reagent for enhancing a chemiluminescent reaction includes luminol or luminol derivatives, an oxidant, an electron mediator, and an enhancer. The enhancer is a nitrogen-containing fused heterocyclic compound having at least two nitrogen atoms. The present disclosure further provides a kit for enhancing a chemiluminescent reaction comprising the foregoing reagent.

16 Claims, 3 Drawing Sheets

REAGENT AND KIT FOR ENHANCING CHEMILUMINESCENT REACTION

BACKGROUND OF THE INVENTION

1. Field of the Invention

The present disclosure relates to a reagent, and particularly to a reagent for enhancing a chemiluminescent reaction.

2. Description of the Related Art

Chemiluminescence immunoassay (CLIA) is an assay that combines chemiluminescence technique with immunochemical reaction, which is available for the detection and analysis of antigens, haptens, antibodies, enzymes, and drugs, etc. In recent years, CLIA has gained increasing attention in various fields such as clinical diagnosis, environmental monitoring, and pharmaceutical analysis because of its high sensitivity, high safety, and good specificity, etc.

Depending on different luminescence mechanisms, CLIA includes direct chemiluminescence immunoassay, chemiluminescence enzyme immunoassay, and electrochemiluminescene immunoassay. Regarding chemiluminescence enzyme immunoassay, an enzyme, such as horseradish peroxidase (HRP), is first used to label an antigen or antibody, after immunoreaction, luminol as a luminescent substrate emits light by oxidation-reduction reaction under the action of the enzyme-labeled immunoreactant and the luminescent reagent, and then the antigen or antibody is determined by luminescence intensity.

Although light emission generated rapidly by the aforementioned reaction, the duration of luminescence is short, resulting in that the stability and reproducibility of the detection results are not good enough. Subsequent studies have found that the use of one or more chemical agents (enhancers) can increase the luminescence intensity and prolong the luminescence time. For example, p-iodophenol is used as an enhancer in Chinese Patent No. CN200410005756.1, and N-azole is used as an enhancer in U.S. Pat. No. 9,040,252B. However, the enhancement of luminescence intensity is still limited.

SUMMARY OF THE INVENTION

An objective of the present disclosure is to provide a reagent for enhancing a chemiluminescent reaction, which can not only effectively enhance the luminescence intensity, but also greatly increase the luminescence time.

To achieve the above objective, a reagent provided in the present disclosure comprises luminol or luminol derivatives, an oxidant, an electron mediator, and an enhancer. The enhancer is a nitrogen-containing fused heterocyclic compound having at least two nitrogen atoms and is a compound selected from:

Preferably, the enhancer is a compound selected from:

-continued

More preferably, the enhancer is or

According to the present disclosure, the oxidant may be hydrogen peroxide or sodium perborate, and preferably sodium perborate.

According to the present disclosure, the electron mediator may be p-iodophenol, p-iodophenylboronic acid, sodium 3-(phenothiazin-10-yl) propane-1-sulfonate (SPTZ), or sodium 4-(phenothiazin-10-yl) butane-1-sulfonate, and preferably SPTZ.

According to the present disclosure, the reagent may have a pH of between 7.0 and 10.0, and preferably between 7.5 and 9.0.

Another objective of the present disclosure is to provide a kit for enhancing a chemiluminescent reaction. The kit comprises a first vial, a second vial, and the reagent of the present disclosure, wherein luminol or luminol derivatives is present in the first vial, the oxidant is present in the second vial, and the electron mediator and the enhancer are present either in the first vial or in the second vial or in both vials. Preferably, the electron mediator and the enhancer are present in the first vial.

According to the present disclosure, the kit may further comprise a peroxidase. The peroxidase may be horseradish peroxidase (HRP), soybean peroxidase, or sweet potato peroxidase, and preferably HRP.

In the kit of the present disclosure, the oxidant may be hydrogen peroxide or sodium perborater, and preferably sodium perborate.

In the kit of the present disclosure, the electron mediator may be p-iodophenol, p-iodophenylboronic acid, sodium 3-(phenothiazin-10-yl) propane-1-sulfonate (SPTZ), or sodium 4-(phenothiazin-10-yl) butane-1-sulfonate, and preferably SPTZ.

In the kit of the present disclosure, the enhancer is a compound selected from:

Preferably, is a compound selected from

-continued

More preferably, is

Because a nitrogen-containing fused heterocyclic compound having at least two nitrogen atoms is used as the enhancer in the reagent of the present disclosure, the intensity of the light emission generated by the chemiluminescent reaction of the reagent and peroxidase can be remarkably enhanced, and the luminescence time can be increased. As such, the reagent of the present disclosure is advantageous in terms of chemical detection, biological detection, immunoassay, etc. utilizing chemiluminescence as a detection means, such as dot blot and Western blot for protein assay, Southern blot and Northern blot for nucleic acid assay, and Enzyme-Linked Immunosorbent Assay (ELISA). As a result, the sensitivity and stability of the chemiluminescence detection technology can be effectively improved.

DETAILED DESCRIPTION OF THE PREFERRED EMBODIMENTS

To make the present disclosure more comprehensible, the present disclosure will be described in further detail below by way of examples in conjunction with the drawings. It is to be understood that the following examples are merely illustrative of the present disclosure and are not intended to limit the present disclosure.

The present disclosure provides a reagent for enhancing a chemiluminescent reaction, which comprises a luminol or luminol derivatives, an oxidant, an electron mediator, and an enhancer. The enhancer is a nitrogen-containing fused heterocyclic compound having at least two nitrogen atoms, and is a compound selected from:

Preferably, the enhancer is a compound selected from:

In one embodiment of the present disclosure, the enhancer is preferably and the enhancer may have a concentration of 1.0 mM to 25.0 mM, and preferably 1.0 mM to 10.0 mM.

In the reagent of the present disclosure, luminol or luminol derivatives used must be of purity suitable and appropriate for luminescence assays. In one embodiment of the present disclosure, luminol or luminol derivatives may be used as sodium salt. The concentration of luminol or luminol derivatives in the reagent of the present disclosure may be between 0.5 mM to 10.0 mM, preferably between 0.5 mM and 1.0 mM, and more preferably 1.0 mM.

In the reagent of the present disclosure, the oxidant may be any substance capable of oxidizing luminol or luminol derivatives to produce light. For example, the oxidant may be sodium perborate or hydrogen peroxide, and in one embodiment of the present disclosure is, but not limited to, sodium perborate. The concentration of the oxidant in the reagent of the present disclosure may be between 0.5 mM to 10.0 mM, preferably between 2.0 mM and 4.0 mM, and more preferably 4.0 mM.

In the reagent of the present disclosure, the electron mediator may be any electroactive substance able to act as electron mediator between the oxidant and the luminol or luminol derivatives. For example, the electron mediator may be benzothiazolea, phenols, aromatic amines, N-alkyl phenothiazinea, indophenols, or arylboronic acids. In one embodiment of the present disclosure, the preferred electron mediators are p-iodophenol, p-iodophenylboronic acid, 3-(phenothiazin-10-yl)propane-1-sulfonate, or 4-(phenothiazine-10-yl)butane-1-sulfonate, and preferably is, but not limited to, sodium 3-(phenothiazin-10-yl) propane-1-sulfonate. The concentration of the electron mediator in the reagent of the present disclosure may be between 0.5 mM and 10.0 mM, preferably between 0.5 mM and 5.0 mM, and more preferably 5.0 mM. Additionally, the electron mediator must not contain impurities that can inhibit the chemiluminescent reaction.

In practical use, the reagent of the present disclosure may be prepared in a kit form to be conveniently used in chemical detection, biological detection, immunoassays, etc. utilizing chemiluminescence as a detection means, such as dot blot, Western blot, Southern blot, Northern blot, and Enzyme-Linked Immunosorbent Assay (ELISA). Specifically, luminol or luminol derivatives and the oxidant are preferably formulated respectively as separate solutions, for example a luminescent solution containing luminol or luminol derivatives and an oxidizing solution containing the oxidant, so as to extend the shelf life.

The electron mediator, the enhancer, and other additives such as a stabilizer may be added to either the luminescent solution or the oxidizing solution, or to both of the two solutions. Both the luminescent solution and the oxidizing solution contain a buffering substance. The buffering substance may be any buffer solution commonly used in the art, such as Tris-HCl buffer solution, phosphate buffer solution, acetate buffer solution, and the like.

In one embodiment of the present disclosure, both the electron mediator and the enhancer are added to the luminescent solution, but not limited thereto; and the buffering substance in the luminescent solution is Tris-HCl buffer solution, and the buffering substance in the oxidizing solution is acetate buffer solution.

When the reagent of the present disclosure is practically used in a chemiluminescent reaction, for example, a chemiluminescence enzyme immunoassay, the luminescent solution is mixed with the oxidizing solution, and a peroxidase is used as a label. The pH of the reagent after the luminescent solution is mixed with the oxidizing solution is between about 8.0 to 9.0. The peroxidase may be any peroxidase suitable for use in luminescence assays. In particular, it may be horseradish peroxidase (HRP), for example Sigma type VI A or IX, or an anionic peroxidase such as soybean peroxidase or sweet potato peroxidase. The peroxidase may be free or conjugated to a ligand, a biopolymer, or a solid phase. In one embodiment of the present disclosure, the horseradish peroxidase Sigma type VI A is used, but not limited thereto.

To make those skilled in the art to fully understand the present disclosure, the present disclosure is now described in more detail below with reference to the following examples and the drawings, but the present disclosure is not limited thereto.

EXAMPLE 1

Effect of Enhancer on Chemiluminescent Emission of Luminol

Luminescent solutions and oxidizing solutions were respectively prepared according to the composition shown in the following Table 1.

TABLE 1

| | Composition | Concentration (mM) |
|---|---|---|
| Luminescent solution | luminol sodium salt | 2.0 |
| | SPTZ | 10.0 |
| Enhancer | 6-chloropurine 2,6-dichloropurine 6-chloroimidazo[1,2-a]pyridine | 10.0 |
| | Tris-HCl buffer solution, pH 9.0 | 300.0 |
| Oxidizing solution | sodium perborate | 8.0 |
| | sodium acetate buffer solution, pH 5.0 | 50.0 |

The prepared luminescent solutions and oxidizing solutions were stored in a refrigerator at 4° C.

The reagents of Experimental Examples 1 to 3 and the Comparative Examples 1 to 3 were prepared respectively as follows.

Reagents of Experimental Examples: A plurality of reagents were prepared by mixing equal parts of the luminescent solutions and the oxidizing solutions shown in Table 1. The pH values of the reagents after mixing were respectively 8.0 to 9.0. The enhancers used in Experimental Examples 1 to 3 were respectively 6-chloropurine, 2,6-dichloropurine, and 6-chloroimidazo[1,2-a]Pyridine.

Reagent of Comparative Example 1: The reagent was prepared in substantially the same manner as in the foregoing Experimental Examples, except that no enhancer is contained.

Reagent of Comparative Example 2: A commercially available luminescent reagent (SuperSignal™ West Femto Maximum Sensitivity Substrate, available from Thermo Fisher Scientific).

Reagent of Comparative Example 3: A commercially available luminescent reagent (Immobilon™ Western Chemiluminescent HRP Substrate, available from Merck Millipore).

A disposable polystyrene black 96-well microplate (supplied by PerkinElmer) is prepared. 180 μL of the reagents of Experimental Examples 1 to 3 and of the reagents of Comparative Examples 1 to 3 were respectively added to each well of the microplate, and then 20 μL of a 10 ng/mL horseradish peroxidase solution (HRP type VI A) was added to each well. The luminescence intensity of the reaction product, 3-aminophthalic acid dianion in the excited state, was recorded every minute for 1 hour by a multifunctional microplate reader (Synergy H1 Hybrid Multi-Mode Microplate Reader, available from BioTek, where a chemiluminescence mode was set, and the detection parameter Gain was set to 130). The results are shown in FIG. 1.

Figure 1:
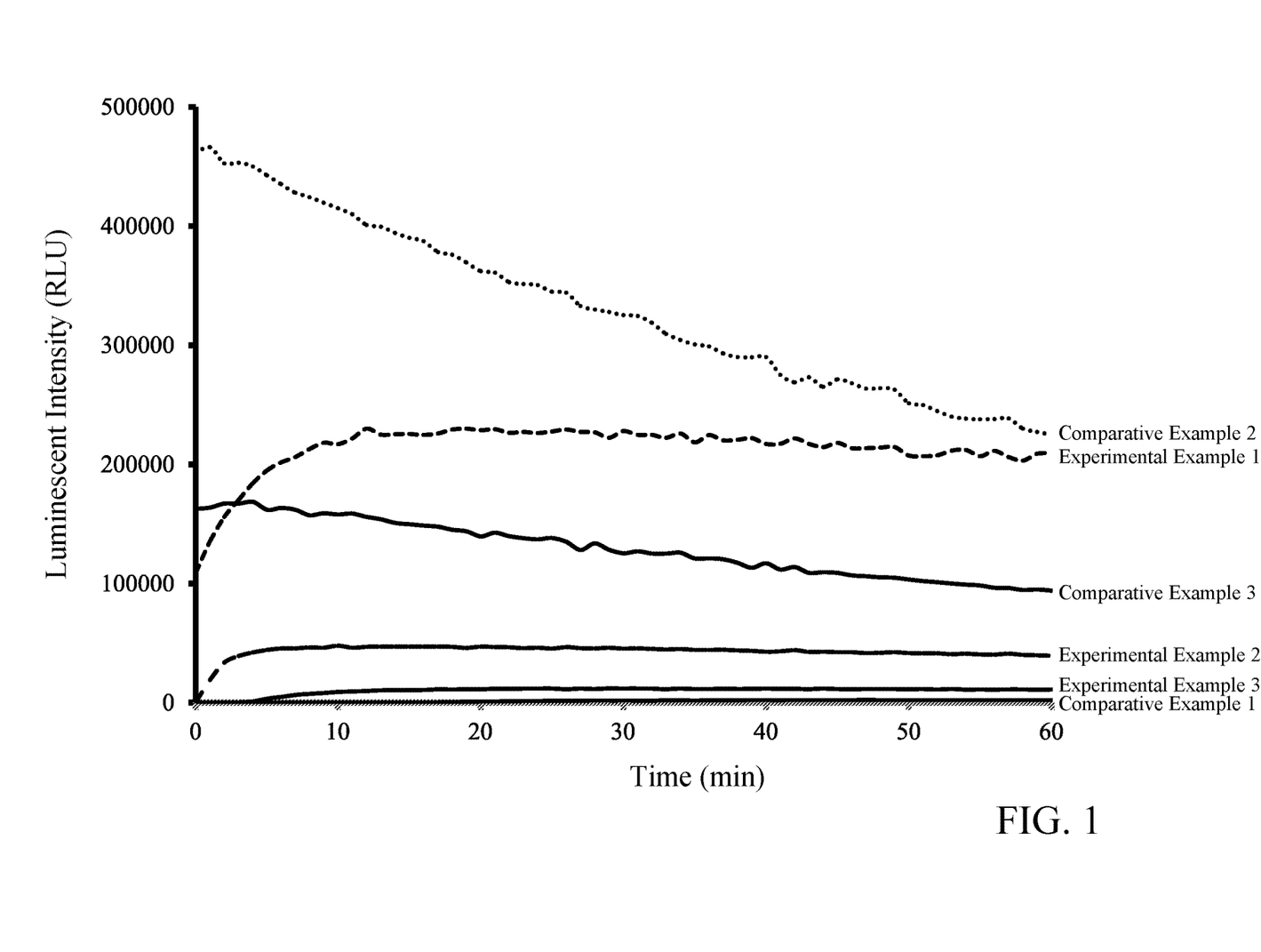
FIG. 1 shows a plot of luminescence intensity versus time for luminol chemiluminescent reactions carried out in the presence of the reagent of the present disclosure and commercially available reagents.

As can be seen from FIG. 1, in comparison with using the reagent of Comparative Example 1 containing no enhancer, the luminescence intensity of luminol chemiluminescent reaction can be effectively enhanced when using the reagent of Experimental Examples 1 to 3, which respectively comprises a nitrogen-containing fused heterocyclic compound having at least two nitrogen atoms as the enhancer. In addition, compared with using the commercially available luminescent agent of Comparative Example 2, the luminescence intensity of luminol chemiluminescent reaction, when using the reagent of Experimental Examples 1 to 3, can be maintained over 60 minutes, whereas the luminescence intensity of luminol chemiluminescent reaction when using the commercially available luminescent agent is significantly decreased with time. Furthermore, in comparison with using the reagent of Comparative Example 3, both the luminescence intensity and stability of luminol chemiluminescent reaction, when using the reagent of Experimental Example 1, can be effectively enhanced and improved.

EXAMPLE 2

Effect of pH of the Reagent on Chemiluminescent Emission of Luminol

Luminescent solutions and oxidizing solutions were respectively prepared according to the composition shown in the following Table 2.

TABLE 2

| | Composition | Concentration (mM) |
|---|---|---|
| Luminescent solution | luminol sodium salt | 2.0 |
| | SPTZ | 10.0 |
| Enhancer | 6-chloropurine 2,6-dichloropurine 6-chloroimidazo[1,2-a]pyridine | 10.0 |
| | Tris-HCl buffer solution, pH 7.0 to 10.0 | 300.0 |
| Oxidizing solution | sodium perborate | 8.0 |
| | ultrapure water | — |

The prepared luminescent solutions and oxidizing solutions were stored in a refrigerator at 4° C.

The reagents of Experimental Examples 1 to 3 and the Comparative Example 1 were prepared respectively as follows.

Reagents of Experimental Examples: A plurality of reagents were prepared by mixing equal parts of the luminescent solutions and the oxidizing solutions shown in Table 2. The pH values of the reagents after mixing were respectively 7.0 to 10.0. The enhancers used in Experimental Examples 1 to 3 were respectively 6-chloropurine, 2,6-dichloropurine, and 6-chloroimidazo[1,2-a]Pyridine.

Reagent of Comparative Example 1: The reagent was prepared in substantially the same manner as in the foregoing Experimental Examples, except that no enhancer is contained.

A disposable polystyrene black 96-well microplate (supplied by PerkinElmer) is prepared. 180 μL of the reagents of Experimental Examples 1 to 3 and of the reagent of Comparative Example 1 were respectively added to each well of the microplate, and then 20 μL of a 10 ng/mL horseradish peroxidase solution (HRP type VI A) was added to each well. The luminescence intensity of the reaction product, 3-aminophthalic acid dianion in the excited state, was recorded every minute for 1 hour by a multifunctional microplate reader (Synergy H1 Hybrid Multi-Mode Microplate Reader, available from BioTek, where a chemiluminescence mode was set, and the detection parameter Gain was set to 130). The determined luminescence intensities were accumulated and the results of accumulated luminescence intensities versus the pHs of the reagents are shown in FIG. 2.

Figure 2:
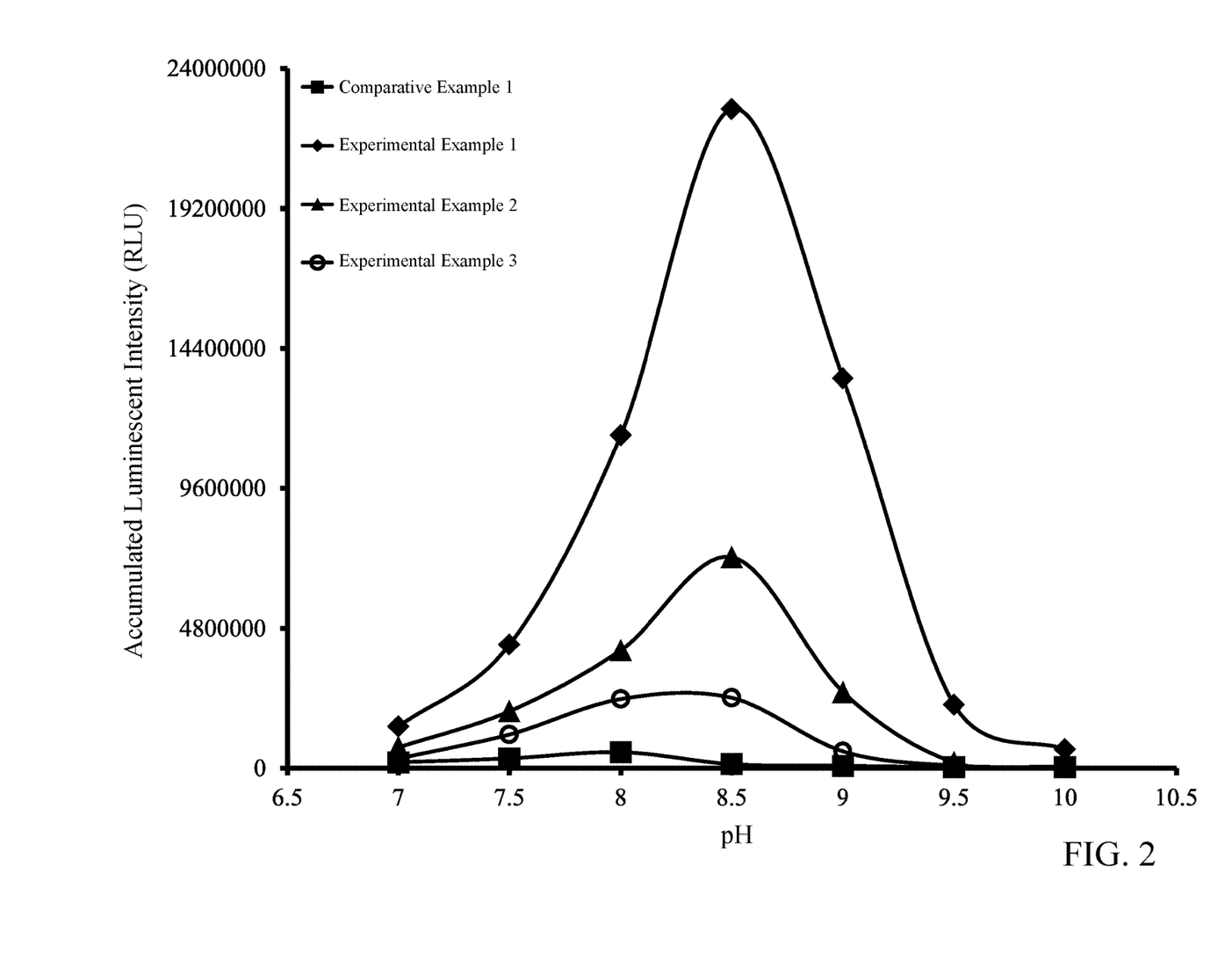
FIG. 2 shows a plot of luminescence intensity versus pH of the reagent of the present disclosure for luminol chemiluminescent reaction carried out in the presence of the reagent of the present disclosure and a commercial reagent.

As can be seen from FIG. 2, in comparison with using the reagent of Comparative Example 1 containing no enhancer, the luminescence intensity of luminol chemiluminescent reaction can be effectively enhanced when using the reagent of Experimental Examples 1 to 3, which respectively comprises a nitrogen-containing fused heterocyclic compound having at least two nitrogen atoms as the enhancer. In the reagent of Experimental Example 1, which uses 6-chloropurine as the enhancer, the luminescence intensity thereof can be effectively enhanced at a pH of the reagent ranging from 7.0 to 10.0. In the reagents of Experimental Examples 2 and 3, which respectively uses 2,6-dichloropurine and 6-chloroimidazo[1,2-a]pyridine as the enhancer, the luminescence intensities thereof can be effectively enhanced at a pH of the reagents ranging from 7.5 to 9.0. In particular, the luminescent intensity can be significantly enhanced at a pH of the reagent ranging from 7.5 to 9.0.

EXAMPLE 3

Effect of Enhancer Concentration on Chemiluminescent Emission of Luminol

Luminescent solutions and oxidizing solutions were respectively prepared according to the composition shown in the following Table 3.

TABLE 3

| | Composition | Concentration (mM) |
|---|---|---|
| Luminescent solution | luminol sodium salt | 2.0 |
| | SPTZ | 10.0 |
| Enhancer | 6-chloropurine | 2.0, 6.0, |
| | 2,6-dichloropurine | 10.0, 20.0, |
| | 6-chloroimidazo[1,2-a]pyridine | 50.0 |
| | Tris-HCl buffer solution, pH 9.0 | 300.0 |
| Oxidizing solution | sodium perborate | 8.0 |
| | sodium acetate buffer solution, pH 5.0 | 50.0 |

The prepared luminescent solutions and oxidizing solutions were stored in a refrigerator at 4° C.

The reagents of Experimental Examples 1 to 3 and the Comparative Example 1 were prepared respectively as follows.

Reagents of Experimental Examples: A plurality of reagents were prepared by mixing equal parts of the luminescent solutions and the oxidizing solutions shown in Table 3. The pH values of the reagents after mixing were respectively 8.0 to 9.0 and the concentrations of the enhancers contained in the reagents were respectively 1.0 mM, 3.0 mM, 5.0 mM, 10.0 mM, and 25.0 mM. The enhancers used in Experimental Examples 1 to 3 were respectively 6-chloropurine, 2,6-dichloropurine, and 6-chloroimidazo[1,2-a]pyridine.

Reagent of Comparative Example 1: The reagent was prepared in substantially the same manner as in the foregoing Experimental Examples, except that no enhancer is contained.

A disposable polystyrene black 96-well microplate (supplied by PerkinElmer) is prepared. 180 μL of the reagents of Experimental Examples 1 to 3 and of the reagent of Comparative Example 1 were respectively added to each well of the microplate, and then 20 μL of a 10 ng/mL horseradish peroxidase solution (HRP type VI A) was added to each well. The luminescence intensity of the reaction product, 3-aminophthalic acid dianion in the excited state, was recorded every minute for 1 hour by a multifunctional microplate reader (Synergy H1 Hybrid Multi-Mode Microplate Reader, available from BioTek, where a chemiluminescence mode was set, and the detection parameter Gain was set to 130). The determined luminescence intensities were accumulated and the results of accumulated luminescence intensities versus the concentrations of the enhancers are shown in FIG. 3.

Figure 3:
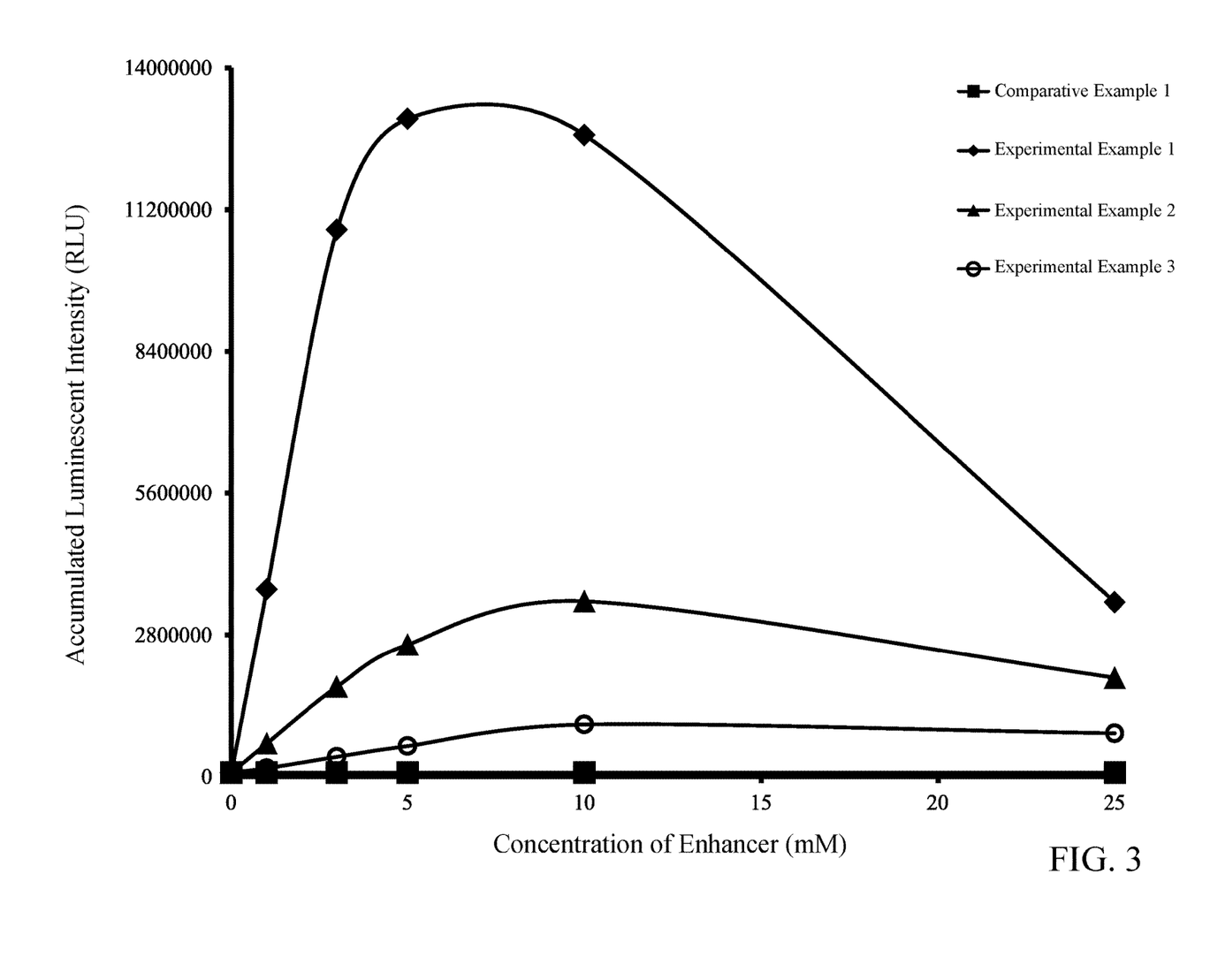
FIG. 3 shows a plot of luminescence intensity versus concentration of enhancer for luminol chemiluminescent reaction carried out in the presence of the reagent of the present disclosure and a commercial reagent.

As can be seen from FIG. 3, in comparison with the reagent of Comparative Example 1 containing no enhancer, the luminescence intensity of luminol chemiluminescent reaction can be effectively enhanced when using the reagent of Experimental Examples 1 to 3, which respectively comprises a nitrogen-containing fused heterocyclic compound having at least two nitrogen atoms as an enhancer. The luminescence intensity can be enhanced at a concentration of the enhancer ranging from 1.0 mM to 25.0 mM. In particular, the luminescent intensity can be significantly enhanced at a concentration of the enhancer ranging from 1.0 mM to 10.0 mM.

The above results confirm that the reagent of the present disclosure can not only significantly enhance the luminescence intensity in the chemiluminescent reaction, but also increase the luminescence time as well as improve the stability of luminescence intensity. Therefore, the reagent of the present disclosure is advantageous in terms of chemical detection, biological detection, immunoassays, etc. utilizing chemiluminescence as a detection means, and the sensitivity and stability of the chemiluminescence detection technique can be effectively improved.

What is claimed is:
1. A reagent for enhancing a chemiluminescent reaction, comprising:
   luminol or luminol derivatives;
   an oxidant;
   an electron mediator; and
   an enhancer, which is a nitrogen-containing fused heterocyclic compound having at least two nitrogen atoms and is a compound selected from the group consisting of:

2. The reagent according to claim 1, wherein the oxidant is sodium perborate or hydrogen peroxide, and the electron mediator is p-iodophenol, p-iodophenylboronic acid, sodium 3-(phenothiazin-10-yl) propane-1-sulfonate, or sodium 4-(phenothiazin-10-yl) butane-1-sulfonate.

3. The reagent according to claim 2, wherein the oxidant is sodium perborate, and the electron mediator is sodium 3-(phenothiazin-10-yl) propane-1-sulfonate.

4. The reagent according to claim 1, wherein the enhancer is a compound selected from the group consisting of:

5. The reagent according to claim 1, wherein the enhancer is:

6. The reagent according to claim 1, wherein the reagent has a pH ranging from 7.0 to 10.0.

7. The reagent according to claim 6, wherein the reagent has a pH ranging from 7.5 to 9.0.

8. A kit for enhancing a chemiluminescent reaction, comprising a first vial, a second vial, and the reagent according to claim 1, wherein the luminol or luminol derivatives is present in the first vial, the oxidant is present in the second vial, and the electron mediator and the enhancer are present either in the first vial or in the second vial or in both vials.

9. The kit according to claim 8, further comprising a peroxidase.

10. The kit according to claim 9, wherein the peroxidase is horseradish peroxidase, soybean peroxidase, or sweet potato peroxidase.

11. The kit according to claim 8, wherein the oxidant of the reagent is sodium perborate or hydrogen peroxide, and the electron mediator of the reagent is p-iodophenol, p-iodophenylboronic acid, sodium 3-(phenothiazin-10-yl) propane-1-sulfonate, or sodium 4-(phenothiazin-10-yl) butane-1-sulfonate.

12. The kit according to claim 8, wherein the oxidant of the reagent is sodium perborate, and the electron mediator of the reagent is sodium 3-(phenothiazin-10-yl) propane-1-sulfonate.

13. The kit according to claim 8, wherein the enhancer of the reagent is a compound selected from the consisting of:

-continued

14. The kit according to claim 13, wherein the enhancer of the reagent is

15. The kit according to claim 8, wherein the reagent has a pH ranging from 7.0 to 10.0.

16. The kit according to claim 15, wherein the reagent has a pH ranging from 7.5 to 9.0.

* * * * *